US008321136B2

(12) United States Patent
Wong et al.

(10) Patent No.: US 8,321,136 B2
(45) Date of Patent: *Nov. 27, 2012

(54) METHOD AND SYSTEM FOR CLASSIFYING SLIDES USING SCATTER PLOT DISTRIBUTION

(75) Inventors: Kam Lin Wong, Bedford, MA (US); Louise Isenstein, Carlisle, MA (US); David Zahniser, Wellesley, MA (US)

(73) Assignee: CYTYC Corporation, Marlborough, MA (US)

( * ) Notice: Subject to any disclaimer, the term of this patent is extended or adjusted under 35 U.S.C. 154(b) by 1347 days.

This patent is subject to a terminal disclaimer.

(21) Appl. No.: 10/794,334

(22) Filed: Mar. 5, 2004

(65) Prior Publication Data

US 2004/0252876 A1 Dec. 16, 2004

Related U.S. Application Data

(60) Provisional application No. 60/478,434, filed on Jun. 12, 2003.

(51) Int. Cl.
*G01N 33/48* (2006.01)
*G06K 9/00* (2006.01)

(52) U.S. Cl. .......................................... 702/19; 382/133

(58) Field of Classification Search ........................ None
See application file for complete search history.

(56) References Cited

U.S. PATENT DOCUMENTS

| 4,097,845 | A | * | 6/1978 | Bacus | 382/134 |
|---|---|---|---|---|---|
| 5,625,705 | A | * | 4/1997 | Recht | 382/128 |
| 5,627,040 | A | * | 5/1997 | Bierre et al. | 435/7.24 |
| 6,137,899 | A | * | 10/2000 | Lee et al. | 382/133 |
| 6,143,512 | A | | 11/2000 | Markovic et al. | |
| 6,716,588 | B2 | * | 4/2004 | Sammak et al. | 435/7.2 |
| 6,944,338 | B2 | * | 9/2005 | Lock et al. | 382/168 |
| 2002/0154798 | A1 | | 10/2002 | Cong et al. | |

FOREIGN PATENT DOCUMENTS

| EP | 0 311 368 | 4/1989 |
|---|---|---|
| WO | WO 02/47032 | 6/2002 |

OTHER PUBLICATIONS

Bacus et al., Applied Optics, 1987, vol. 26, No. 16, p. 3280-3293.*
Kopp et al., The Journal of Histochemistry and Cytochemistry, 1974, vol. 22, No. 7, p. 598-604.*
Turner et al., University of Huddersfield, Queensgate, UK, 1999, p. 1-12.*
Bjelkenkrantz et al., Histochemistry, 1981, vol. 73, p. 353-362.*
Rosner et al. (Fundamentals of Biostatics, 5th Edition, Copyright 2000, p. 1-19).*
Ellis et al. (Image and Vision Computing archive, 1992, vol. 10 , Issue 5, p. 271-276).*
Asano et al. (Transactions of the Institute of Electronics, Information and Communication Engineers D , 1988, vol. J71D , No. 1 , pp. 118-125).*
Greenfield et al. (The American Journal of Sports Medicine, 1998, vol. 26, No. 2, p. 34-39).*
PCT International Search Report for PCT/US04/015834, Applicant: Cytyc Corporation, Forms PCT/ISA/210 and 220, dated Nov. 25, 2004 (7 pages).
PCT Written Opinion of the International Search Authority for PCT/US04/015834, Applicant: Cytyc Corporation, Form PCT/ISA/237, dated Nov. 25, 2004 (5 pages).
Examination Report from Australian Patent Office, Form APO/SG/409, for Singapore Application No. SG 2005007721-9, Applicant Cytyc Corporation. (4 pages).
Bjelkenkrantz, K., et al., HISTOSCAN: Computer Program for Cytophotometry in Tissue Sections in its Application in the Evaluation of Nuclear Atypia, Histochemistry (1981) 73:353-362.
Non-Final Office Action dated Nov. 29, 2007 from U.S. Appl. No. 10/795,012, filed Mar. 5, 2004, Inventor: Kam Lin Wong (13 pages).

* cited by examiner

*Primary Examiner* — Pablo Whaley
(74) *Attorney, Agent, or Firm* — Vista IP Law Group LLP (57) ABSTRACT

The present invention relates to a method and system for classifying biological specimen. A number of objects of interest are identified in a biological specimen. The nuclear area and nuclear integrated optical density for each object of interest in the specimen are measured and used for generating a scatter plot. The specimen is classified as normal or suspicious based on the distribution of points within the scatter plot.

81 Claims, 4 Drawing Sheets

METHOD AND SYSTEM FOR CLASSIFYING SLIDES USING SCATTER PLOT DISTRIBUTION

RELATED APPLICATIONS

This application claims priority from provisional U.S. patent application Ser. No. 60/478,434, filed Jun. 12, 2003.

FIELD OF THE INVENTION

The field of the present invention generally relates to methods and systems for analyzing biological specimens, and more particularly to methods and systems for classifying biological specimens as normal, abnormal or suspicious, and determining the stain quality of such specimens.

BACKGROUND OF THE INVENTION

In the medical industry, there is often a need for a laboratory technician, e.g., a cytotechnologist, to review a cytological specimen for the presence of specified cell types. For example, there is presently a need to review a cervico-vaginal Papanicolaou (Pap) smear slides for the presence of malignant or pre-malignant cells. Since its introduction over fifty years ago, Pap smears have been a powerful tool for detecting cancerous and precancerous cervical lesions. During that time, the Pap smear has been credited with reducing mortality from cervical cancer by as much as 70%. This once precipitous drop in the death rate has slowed however, and the mortality rate in the United States for this preventable disease has remained virtually constant, at about 5,000 per year since the mid-eighties. Therefore, about one-third of the 15,000 women diagnosed with cervical cancer annually still die, because the cancer was detected too late. A further cause for concern is National Cancer Institute data that shows an annual 3% increase in the incidence of invasive cervical cancer in white women under 50 years of age since 1986.

A number of factors may be contributing to this current threshold, not the least of which is the fact that many women, particularly in high risk populations, are still not participating in routine cervical cancer screening. Another contributing factor that has received much attention is the limitation of the traditional Pap smear method itself.

The reliability and efficacy of a cervical screening method is measured by its ability to diagnose precancerous lesions (sensitivity) while at the same time avoiding false positive diagnosis (specificity). In turn, these criteria are dependent on the accuracy of the cytological interpretation. Traditionally, a pathologist may perform a single cell analysis on a biological specimen by looking at the characteristics of individual cell nuclei, or a contextual analysis on the biological specimen by looking for characteristic patterns in the architecture of the cells as they appear on the slide.

Even when performing both single cell and contextual analyses, the conventional Pap smear has false negative rates ranging between 10-50%. This is due in large part to the vast number of cells and objects (typically as many as 100,000 to 200,000) that must be reviewed by a technician to determine the possible existence of a small number of malignant or pre-malignant cells. Thus, Pap smear tests, as well as other tests requiring detailed review of biological material, have suffered from a high false negative rate due to fatigue imposed on the technician.

To facilitate this review process, automated screening systems have been developed. In a typical system, an imager is operated to provide a series of images of a cytological specimen slide, each depicting a different portion of the slide. A processor then processes these images to furnish quantitative and prognostic information about the specimen. The processor can perform either a single cell analysis or a contextual analysis, or both, in providing this diagnostic information. For example, when performing a single cell analysis, the processor may determine such cell characteristics as cytoplasmic area ratio, nuclear integrated optical density, average nuclear optical density, nuclear texture, and cytoplasmic hue. When performing a contextual analysis, the processor may determine such architectural characteristics as (1) average internuclear distances within clusters; (ii) standard deviation of the cytoplasmic grey values; (iii) means of the area of bare nuclei; (iv) standard deviation of the area of the bare nuclei; (v) average cytoplasm area of clusters; and (vi) inverse inter-cell distances. The results of the single cell and contextual analyses are combined to arrive at a diagnosis that is generally more accurate than if only one of the cell and contextual analyses formed the basis for the diagnosis.

In some automated screening systems, the processor uses the diagnostic information to delineate between "normal" and "suspicious" slides. In the clinical laboratory, only those slides flagged as suspicious would be examined by a cytotechnologist, thus reducing the work load. In other automated screening systems, the processor uses the diagnostic information to delineate between normal and suspicious biological material within each specimen. That is, the processor will focus the cytotechnologist's attention on the most pertinent cells, with the potential to discard the remaining cells from further review. In this case, the screening device uses the diagnostic information to determine the most pertinent biological objects (e.g., the cells and cell clusters mostly likely to have attributes consistent with malignant or pre-malignant cells), and their locations on the slide. This location information is then passed onto a microscope, which automatically proceeds to these locations and centers on the biological objects for review by the cytotechnologist. The cytotechnologist will then electronically mark the biological objects that are the most pertinent (for example, the objects having attributes consistent with malignant or pre-malignant cells) for further review by a pathologist.

In general, the use of automated screening systems has proved to be successful; since the technician's attention is focused on the those slides that are suspicious or on a limited number of more pertinent objects within each slide. No automated device, however, has thus far eliminated false negative and false positive results at sufficiently low cost to be practical. In addition, there is also a commercial aspect that must be taken into account. The cost borne by laboratories to review cytological specimens, such as Pap smear specimens, is tied, at least in part, to the time taken for a technician to review each slide. That is, the more slides that a cytotechnologist must review, or the more time it takes for a technician to review each slide slide, the more cost in labor the laboratory incurs. Conversely, the less slides that a technician must review, and the less time that it takes for the technician to review a slide, the more money the laboratory can save.

The occurrence of false positives sometimes results from biological specimens with low-quality stains. For example, a technician may fail to follow the proper protocol for applying a particular stain to the biological specimens, or if correctly applied, the shelf-life of the stain may have expired. Oftentimes, specimens are not flagged as having a low-quality stain until after they have been manually reviewed by the cytotechnologist, thereby wasting valuable time.

There thus remains a need to provide a more efficient and accurate process for analyzing biological specimens, such as Pap smear specimens, and determining the stain quality of such biological specimens.

SUMMARY OF THE INVENTION

In accordance with one aspect of the invention, a method of classifying a biological specimen comprises identifying a number of objects of interest (OOIs) within the biological specimen. In a preferred method, this can be accomplished by acquiring images of the biological specimen and processing the images to identify OOIs. The method further comprises measuring a first (e.g., nuclear area) and a second (e.g., nuclear integrated optical density (IOD)) feature of each OOI, and then generating a scatter plot of the measured first features versus the measured second features. The specimen is then classified (e.g., as normal or suspicious) based at least in part on a distribution of points within the scatter plot. In one embodiment, the specimen is classified as normal based on a spread of the point distribution, which is relatively small in the case of a specimen exhibiting normal cellular attributes, and relatively large in the case of a specimen exhibiting abnormal cellular attributes. In this case, the specimen will be classified as normal if the point distribution spread is below a threshold. The specimen may also be classified as suspicious at least partially based on a distribution of points within the scatter plot. In this case, the specimen will be classified as suspicious if the point distribution spread is above a threshold. This classification can be applied in any one of a variety of scenarios, e.g., to remove normal slides from subsequent review or providing a standard for other devices.

In a preferred method, normal specimens are flagged as not requiring further review, in which case, subsequent review of the specimen can be conveniently passed, thereby reducing the number of slides that a cytotechnologist must review. In contrast, a suspicious specimen is flagged as requiring further review. Subsequent review of the specimen can be performed in any one of a variety of manners, but in the preferred method, a plurality of fields of interest that include the OOIs are generated in order to focus the cytotechnologist's attention on the suspicious objects.

In a preferred method, the point distribution spread is quantified using any one of a variety of techniques. For example, the quantification step can comprise fitting a geometric shape (e.g., an ellipse) to the points, determining at least one of the dimensions of the geometric shape, and computing a value that is a function of the dimension(s). For example, a composite score (in the case of two dimensions) can be computed. The computed value can then be compared to the threshold value.

The preferred method can optionally comprise measuring at least one additional feature of the specimen, wherein the specimen is classified as normal based further on the additional measured feature(s). By way of non-limiting example, this additional information can be used to determine if the scatter plot is reliable. The additional feature can be any suitable feature including the total number of OOIs in the specimen, total number of artifacts in the specimen, and mean nuclear optical density of the OOIs.

In accordance with a second aspect of the invention, a biological screening system for classifying a biological specimen is provided. The system comprises an imaging station for obtaining images of the specimen and generating image data from the images. The system further comprises at least one processor for processing (e.g., filtering) the image data to identify a number of OOIs within the biological specimen, measuring a first feature of each OOI, measuring a second feature of each OOI, generating a scatter plot of the first measured feature versus the second measured feature, and classifying the specimen at least in part based on the spread of the point distribution. These functions can be performed in the same manner as previously described above. If fields of interest (FOIs) are optionally generated, the system comprises an automated or semi-automated reviewing station for scanning a field of view (FOV) relative to each FOI to present the one or more OOIs in each FOI.

BRIEF DESCRIPTION OF THE DRAWINGS

The drawings illustrate the design and utility of preferred embodiments of the present invention, in which similar elements are referred to by common reference numerals, and in which.

DETAILED DESCRIPTION OF THE PREFERRED EMBODIMENTS

Figure 1:
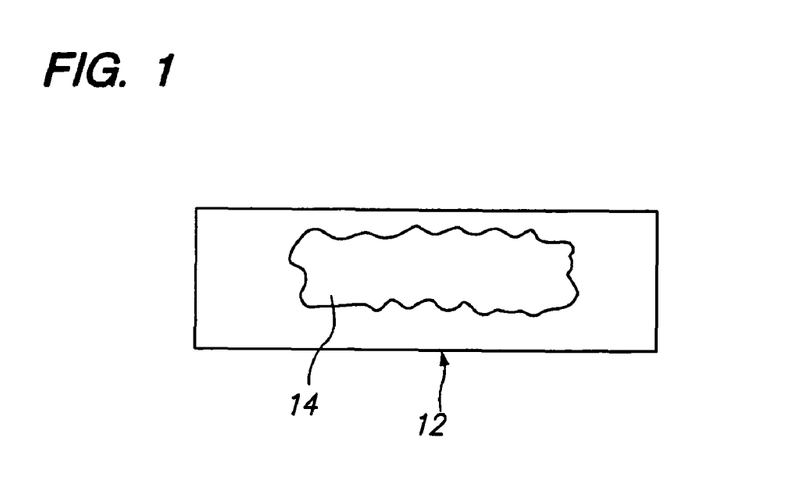
FIG. 1 is a plan view of a standard microscope slide carrying a biological specimen.
Figure 2:
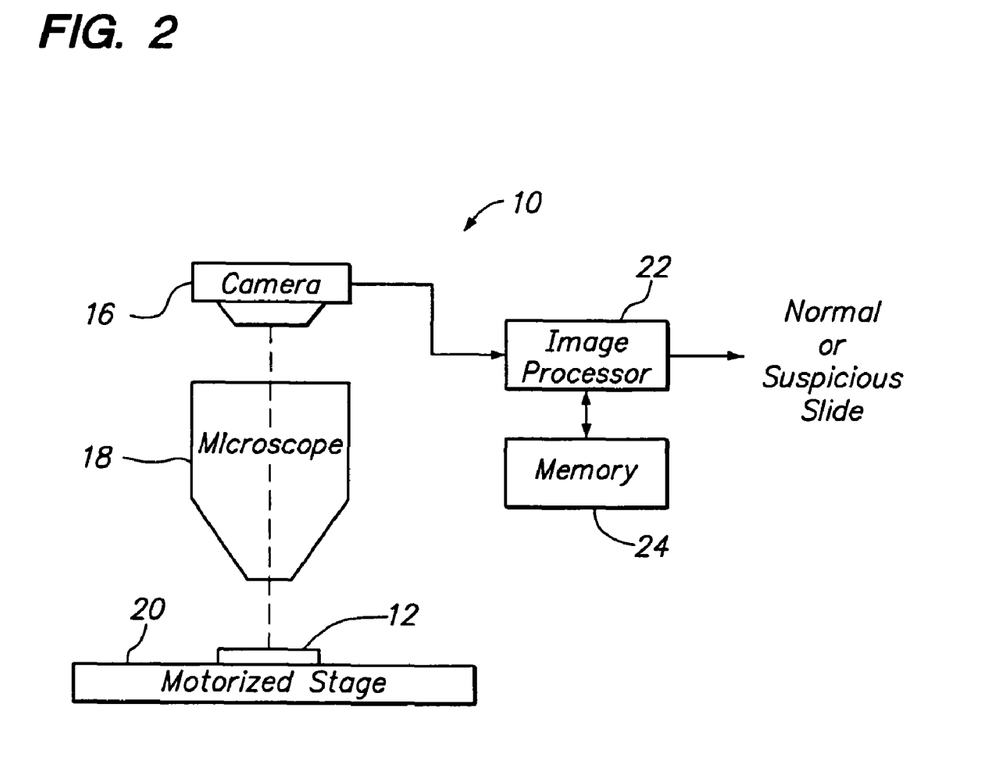
FIG. 2 is a plan view of a biological screening system constructed in accordance with one preferred embodiment of the present invention.

Referring to FIG. 2, a biological screening system 10 constructed in accordance with one preferred embodiment of the present invention is described. The system 10 is configured to process a series of microscope slides 12 in order to classify a biological specimen 14 (best shown in FIG. 1) as either "normal," which would not require review by a cytotechnologist, or "suspicious," which would require review by the cytotechnologist.

Although the system 10 can be used to classify any biological specimen as normal or suspicious, the system 10 lends itself particularly well to the presentation of cytological cervical or vaginal material, such as that typically found on a Pap smear slide. In this case, the cells may reflect abnormalities (e.g., cytolysis, atrophy, infection, damage), malignancy or premalignancy, such as Low Grade Squamous Intraepithelial Lesions (LGSIL) or High Grade Squamous Intraepithelial Lesions (HGSIL), as well as all other cytologic categories as defined by The Bethesda System for Reporting Cervical/Vaginal Cytologic Diagnosis. The biological specimen 14 will typically be placed on the slide 12 as a thin cytological layer. Preferably, a cover slip (not shown) is adhered to the specimen 14, thereby fixing the specimen 14 in position on the slide 12. The specimen 14 may be stained with any suitable stain, such as a Papanicolaou stain.

During processing, the system 10 obtains images of biological specimens 14 carried by slides 12, which are typically contained within a cassette (not shown). During the imaging process, the slides 12 are removed from the respective cassettes, digitally imaged, and then returned to the cassettes in a serial fashion. Then, the system 10 analyzes the digital images (either serially as each slide is processed, or offline when processing of all slides is complete) in order to classify the specimens 14 as either being normal or suspicious.

In performing the imaging operation, the system 10 comprises a camera 16, a microscope 18, and a motorized stage 20. The camera 16 captures magnified images of the slide 12 through the microscope 18. The camera 16 may be any one of a variety of conventional cameras, such as a charge coupled device (CCD) camera, which alone or in conjunction with other components, such as an analog-to-digital (A/D) converter, can produce a digital output of sufficient resolution to allow processing of the captured images, for example a digital image having a resolution of 640×480 pixels. Preferably, each pixel is converted into an eight-bit value (0 to 255) depending on its optical transmittance, with "00000000" being the assigned value for least amount of light passing through the pixel, and "11111111" being the assigned value for a greatest amount of light passing through the pixel. The slide 12 is mounted on the motorized stage 20, which scans the slide 12 relative to the viewing region of the microscope 18, while the camera 16 captures images over various regions of the biological specimen 12. The shutter speed of the camera 16 is preferably relatively high, so that the scanning speed and/or number of images taken can be maximized.

In performing the analysis function, the system 10 comprises an image processor 22 that performs a variety of operations on the digital images obtained from the camera 16. In the preferred embodiment, the image processor 22 performs primary segmentation, secondary segmentation, classification, and contextual analysis operations to determine if each slide 12 is normal or suspicious.

In the primary segmentation operation, the image processor 22 removes artifacts from further consideration. The image processor 22 accomplishes this by masking pixels in the digital image from further consideration that, by virtue of their lightness, are unlikely to be cell nuclei. The remaining pixels in the digital image form "blobs" having all manner of shapes and sizes. The image processor 22 then performs an erosion process on the blobs in order to remove from further consideration blobs that are only a few pixels in diameter and narrow strands extending from blobs or connecting adjacent blobs. The image processor 22 then determines whether each blob in the image is an individual object or a clustered object, depending on the number of pixels in the blob. For example, a blob having more than 590 pixels can be considered a clustered object, whereas a blob having 590 or less pixels can be considered an individual object. For individual objects, blobs that do not meet certain criteria related to total area, perimeter to area ratio, optical density standard deviation, and grayscale mean pixel value are not considered further.

In the secondary segmentation operation, the image processor 22 removes blobs that are unlikely to be individual cells or clustered cells. For individual objects, the image processor 22 performs a series of erosion operations, which remove small objects and eliminates projections from the remaining blobs, and dilation operations, which remove holes from the remaining blobs. For clustered objects, the image processor 22 sharpens the edges of the object to provide a defined border. From the defined clustered object, the image processor 22 then selects an individual object having the highest nuclear integrated optical density (IOD) and that satisfies a particular shape requirement. The individual objects extracted from clustered objects will be flagged as cluster-extracted objects.

In the classification operation, the image processor 22 measures various features for each of the individual objects and clustered objects, and then calculates an object score for each object based on the measured values of these features. Based on this score, the image processor 22 removes individual objects and clustered objects that are likely to be artifacts. The remaining individual objects are considered objects of interest (OOIs). The image processor 22 then evaluates the OOIs for their nuclear IOD (either corrected or uncorrected), and ranks the OOIs in accordance with the IOD values. The image processor 22 also measures the nuclear area of each of the OOIs for the contextual analysis, described below. For each digital image, the image processor 22 then stores the OOIs, along with their ranking, and measured nuclear areas and nuclear IODs, within the memory 24 as a frame data record (FDR). In the illustrated embodiment, approximately 2000 digital images are obtained for each slide 12, and thus approximately 2000 FDRs will be stored in memory 24 for each slide 12.

In the contextual analysis operation, the image processor 22 obtains from the FDRs, the nuclear area and nuclear IOD's of the 100 highest ranked OOIs, and generates a scatter plot of the nuclear area (y-axis) versus the nuclear IOD (x-axis) of each of the OOIs. For example, the scatter plot illustrated in FIG. 3 was generated from a slide carrying a biological specimen with normal cells, whereas the scatter plot illustrated in FIG. 4 was generated from a slide carrying a biological specimen with abnormal cells. Based on this scatter plot, the image processor 22 will either classify the specimen 14 as normal and flag the biological specimen 14 as not requiring further review by a cytotechnologist, or classify the specimen 14 as suspicious and flag the biological specimen 14 as requiring further review by a cytotechnologist.

Figure 3:
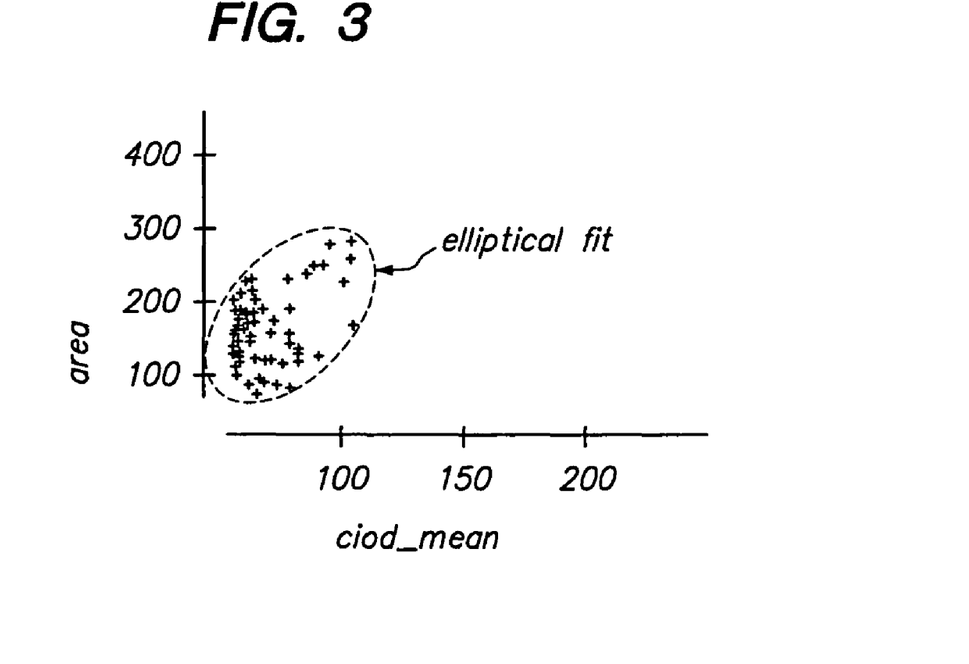
FIG. 3 is a scatter plot of the nuclear area (y-axis) versus the nuclear integrated optical density (x-axis) of objects of interest found in a normal biological specimen.
Figure 4:
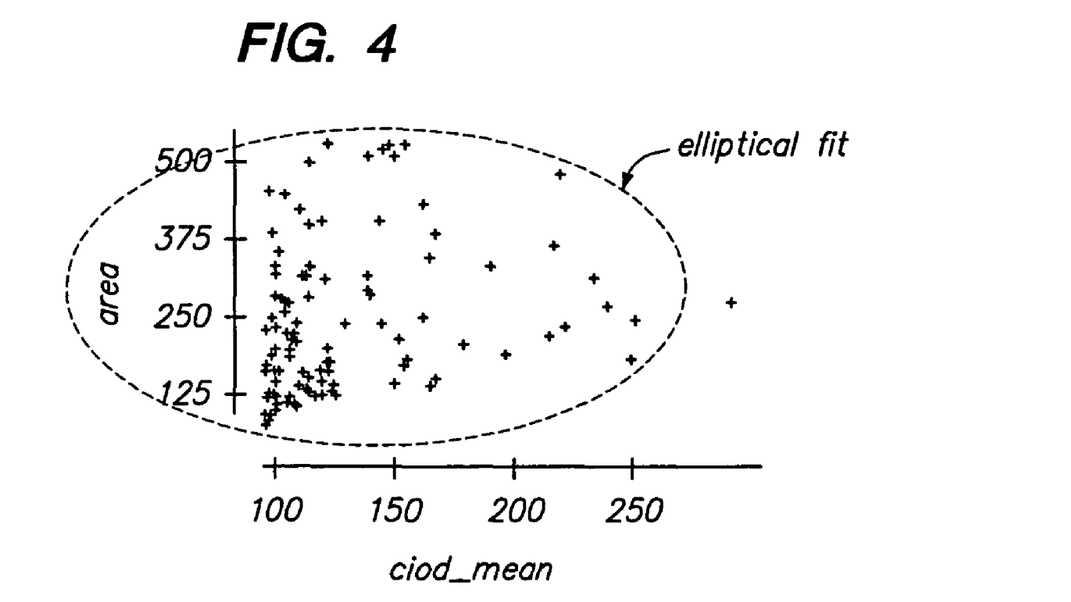
FIG. 4 is a scatter plot of the nuclear area (y-axis) versus the nuclear integrated optical density (x-axis) of objects of interest found in a suspicious biological specimen.

In general, biological specimens that contain cells that reflect abnormalities tend to have a wider distribution in terms of both nuclear area and nuclear IOD (i.e., the scatter points tend to form a loosely bounded region), as illustrated in FIG. 4. In contrast, biological specimens that contain normal cells tend to have a narrow distribution in terms of both nuclear area and nuclear IOD (i.e., the scatter points tend to form a tightly bounded region), as illustrated in FIG. 3. Thus, the spread of the scatter point distribution provides an indication of whether the biological specimen 14 located on the slide 12 is normal or suspicious. The difference in the scatter plots illustrated in FIGS. 3 and 4 stems from the fact that abnormal cells will tend to have larger nuclear areas and higher nuclear IODs (by virtue of increased amount of chromatin) than normal cells, and thus will spread the scatter points away from the otherwise well-defined region defined by the scatter point distribution resulting from normal cells.

The scatter point distribution can be quantified using any one of a variety of methods, but in the preferred embodiment, a geometric fit is performed on the scatter points, as illustrated in FIGS. 3 and 4. Notably, the scatter point distribution from a normal slide will tend to be somewhat elliptical, and thus an elliptical fit is preferred. Using the general principle that the biological specimen incrementally becomes more suspicious as the scatter point distribution varies from this tightly bound elliptical shape, the size of the ellipse, as measured by its minor and major axes, will provide an indication of whether the biological specimen is normal or suspicious. In the preferred embodiment, the dimensions of the major and minor axes are weighted and used to calculate a composite score.

Once the score has been computed, it is compared against a threshold value. Assuming that the score is computed in a manner such that the suspicion of a biological specimen increases as the score increases, a score higher than the threshold value will indicate that the biological specimen is suspicious, while a score lower than the threshold value will indicate that the biological specimen is normal. In this case, the image processor 22 will classify the specimen 14 as normal if the score is less than the threshold value, and will classify the specimen 14 as suspicious if the score is greater than the threshold value.

Significantly, selection of the threshold value depends on two competing factors: the generation of false negatives (i.e., slides containing abnormal cells that have been identified as normal) and the generation of false positives (i.e., slide containing normal cells that have been identified as suspicious). In general, the generation of false negatives is less tolerable than the generation of false positives, since the possibility of misdiagnosing disease weighs heavily against the possibility of requiring unnecessary review by a cytotechnologist. Given this, the threshold value is preferably selected, such that the percentage of false negatives is maintained at a low level, e.g., 5%, while allowing the percentage of false positives to increase to a high level, e.g., 50%. Although, in this case, twice as many slides than necessary are subsequently reviewed, the reduction in the number of slides actually reviewed by the cytotechnologist has been cut in half.

Notably, the limitation of the number of OOIs analyzed (i.e., only 100 OOIs are used to generate the scatter plot), not only reduces processing requirements, but also helps to safeguard against false negatives, since the scatter plot will presumably be generated from an enriched set of suspicious OOIs.

To further minimize false negatives, additional information can be used to ensure that the scatter plot generated from the highest ranked OOIs is reliable. For example, a scatter plot based on the nuclear areas and nuclear IODs of all OOIs can be generated, and used to generate another score. This score, like the score derived from the scatter plot generated from the highest ranked OOIs, can be compared to a threshold value and used to determine whether the specimen 14 should be classified as normal or suspicious. In this case, if either of the scores from both scatter plots are above the respective threshold values, the specimen 14 will be classified as suspicious. Thus, for the specimen 14 to be classified as normal both scores must be below the respective threshold values. Alternatively, the scores derived from both scatter plots can be weighted and combined into a total score, which can then be compared to a single threshold value.

Other information can be used to determine if the scatter plot generated from the highest ranked OOIs is reliable. For example, the number of artifacts in the biological specimen, an elevated number of which may result in a deceptive score, can be measured and compared against a threshold value. If the number of artifacts is above this threshold value, the specimen 14 may be classified as suspicious, even though the score derived from the scatter plot may indicate that the slide 12 is normal.

Also, the number of OOIs can be measured and compared to a threshold value or a threshold range. For example, a relatively small number of OOIs may indicate that the pool of OOIs from which the scatter plot was generated is statistically too small to provide accurate results. Or a relative large number of OOIs may result in a large number of artifacts that may skew the results obtained from the scatter plot. In this case, if the number of OOIs is less than a low threshold value or greater than a high threshold value, i.e., the number of OOIs falls outside of a threshold range, the specimen 14 may be classified as suspicious, even though the score derived from the scatter plot may indicate that the slide 12 is normal.

The mean optical density (either corrected or not) of small OOIs or all OOIs can be measured and compared against a threshold value or threshold range. For example, a relatively low optical density may indicate that the specimen was not sufficiently stained, whereas a relatively high optical density may indicate that the specimen was overly stained. Either case may skew the nuclear IOD measurements, thereby creating a deceptive score. In this case, if the mean optical density is less than a low threshold value or greater than a high threshold value, i.e., the mean optical density falls outside of a threshold range, the specimen 14 may be classified as suspicious, even though the score derived from the scatter plot may indicate that the slide 12 is normal.

It should be noted that the system 10 can classify specimens for purposes other than determining whether a slide should be reviewed by a cytotechnologist. For example, normal specimens, as classified by the system 10, can be used to standardize equipment, such as screening systems that require the cytotechnologist to review all slides. For example, the normal specimens can be processed through the screening system to provide a standardized mean nuclear optical density. Subsequent unprocessed specimens can then be processed through the screening system. If the subsequent specimens have measured mean nuclear optical densities that vary from the standardized mean nuclear optical densities a given amount (e.g., if the subsequent specimens have been stained too much or too little), the results will be rejected.

The use of scatter plots can also be used by screening systems that delineate between normal and suspicious cellular material within each specimen. Specifically, with reference to FIG. 6, a biological screening system 110 constructed in accordance with another preferred embodiment of the present invention is described. The screening system 110 is generally the same as the previously described system 10, with the exception that the system 110 requires the cytotechnologist to subsequently review all slides 112 (one shown in FIG. 5), focusing the cytotechnologist's attention only on those regions of the specimen 114 (referred to as fields of interest (FOIs)) that are suspicious. That is, no slides 112 (even if suspicious) are discarded prior to review by a cytotechnologist. The system 110 uses a scatter plot to indicate which slides 112 are suspicious, thereby cautioning the cytotechnologist to pay particular attention to the suspicious slides.

Figure 6:
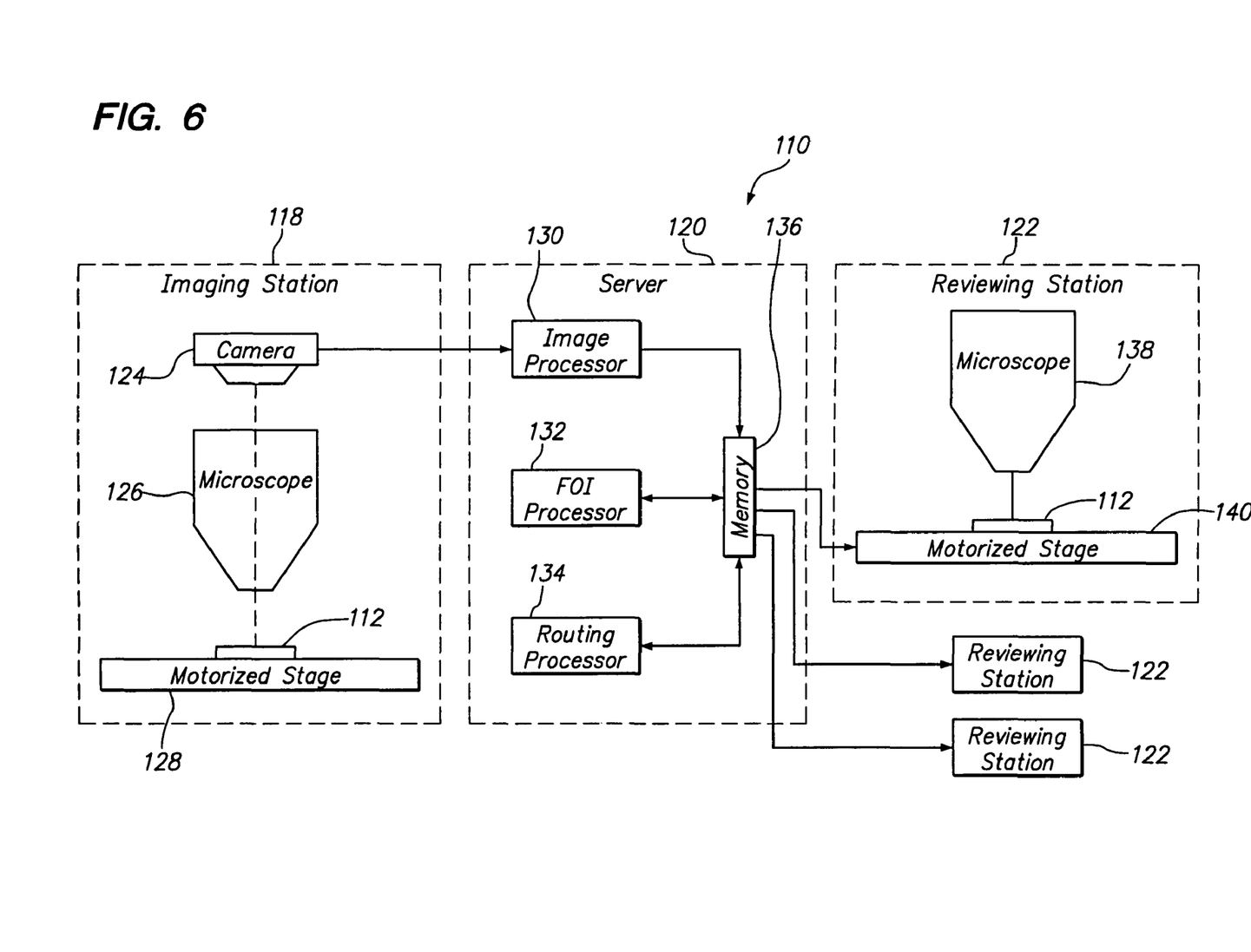
FIG. 6 is a plan view of a biological screening system constructed in accordance with another preferred embodiment of the present invention.

The system 110 generally comprises (1) an imaging station 118 for obtaining scanned images of the biological material contained on the slide 112 and generating electronic image data from the images; (2) a server 120 for filtering the image data to obtain the OOIs and for assigning one or more of the OOIs to each FOI; and (3) a plurality of reviewing stations 122 (3 shown), each of which provides a field of view (FOV) (illustrated in FIG. 7) that is scanned relative to each FOI in order to present the OOIs to the cytotechnologist. The system 110 may also comprise a user interface (not shown), including a monitor, keyboard, and mouse (all not shown), so that the cytotechnologist can interact with the system 110.

The imaging station 118 is configured to image the slide 112 in a manner similar to that described above with respect to the screening system 10. To this end, the imaging station 118 comprises a camera 124, microscope 126, and motorized stage 128 that are similar to the camera 16, microscope 18, and motorized stage 20 described above. The motorized stage 128, however, additionally keeps track of the x-y coordinates of the images as they are captured by the camera 124. For example, encoders (not shown) can be coupled to the respective motors of the motorized stage 128 in order to track the net distance traveled in the x- and y-directions during imaging.

Figure 5:
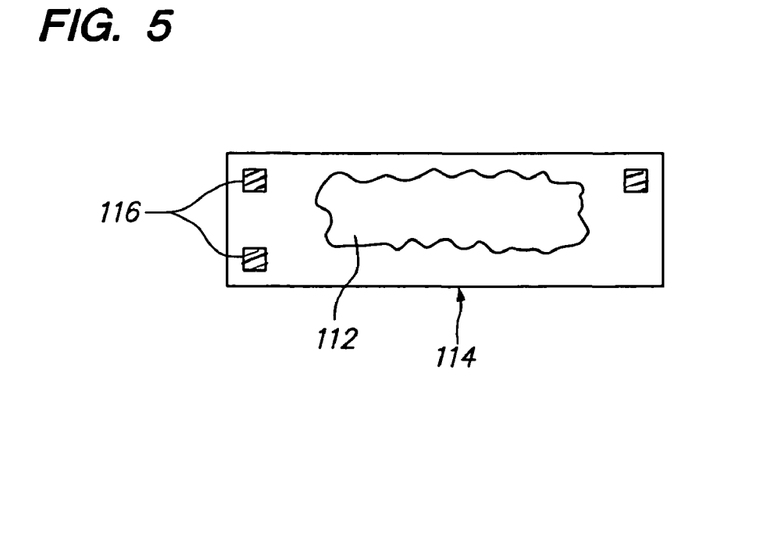
FIG. 5 is a plan view of another standard microscope slide carrying a biological specimen.

These coordinates are measured relative to fiducial marks 116 affixed to the slide 112 (shown in FIG. 5). As will be described in further detail below, these fiducial marks 116 will also be used by each reviewing station 122 to ensure that the x-y coordinates of the slide 112 during the review process can be correlated with the x-y coordinates of the slide 112 obtained during the imaging process.

The server 120 comprises (1) an image processor 130 that is configured to obtain the OOIs from the image data acquired from the camera 124; (2) a FOI processor 132, which is configured to assign OOIs to each FOI; (3) a routing processor 134, which is configured to map a routing path that the reviewing station 122 will use to scan from one FOI to the next; and (4) memory 136 configured for storing the OOIs and FOIs, the ranking and x-y coordinates of the OOIs, and the routing path for the FOIs. It should be appreciated that the functions performed by the respective processors 132, 134, and 136 can be performed by a single processor, or alternatively, performed by more than three processors. Likewise, it can be appreciated that the memory 136 can be divided into several memories.

The image processor 130 is similar to the previously described image processor 22, with the exception that it ranks the ABCs (i.e., the abnormal clusters) and stores the ABCs, along with their rankings, with the FDRs. The image processor 130 additionally stores the coordinates of the OOIs and ABCs within the FDRs. In the same manner as the image processor 22, the image processor 130 obtains from the FDRs, the nuclear area and nuclear IOD's of the 100 highest ranked OOIs, and generates a scatter plot of the nuclear area (y-axis) versus the nuclear IOD (x-axis) of each of the OOIs. The image processor 130 then classifies the slide 112 as normal or suspicious based on the scatter plot, and optionally any additional information. If the slide 112 is classified as suspicious, the image processor 130 will store a flag in memory 112 indicating so.

The FOI processor 132 defines FOIs based on the x-y coordinates of the OOIs. In the illustrated embodiment, 22 FOIs are defined, 20 of which are reserved for OOIs, and 2 of which are reserved for ABCs, i.e., abnormal clusters. In the simplest case, 20 of the FOIs are centered over the 20 highest ranked OOIs, and the remaining 2 FOIs are centered over the 2 highest ranked ABCs. Alternatively, the FOIs are defined in a manner that avoids inclusion of OOIs and ABCs in an FOI that are already included within another FOI. In this manner, the OOIs and ABCs can be grouped within the FOIs in a coordinated manner, so that the number of OOIs and ABCs that are included within FOIs can be maximized. Alternatively, if the number of FOIs is not fixed, the number of FOIs required to include all of the OOIs and ABCs can be minimized. Further details on this alternative method of defining FOIs is described in copending U.S. patent application Ser. No. 10/866,397, entitled "Method and System for Organizing Multiple Objects of Interest in Field of Interest," which is expressly incorporated herein by reference.

After the FOIs have been generated, the FOI processor 134 stores the x-y coordinates of all of the FOIs in memory 138 for later use by the routing processor 136. Specifically, the routing processor 136 maps the x-y coordinates of the FOIs using a suitable routing algorithm, such as a "traveling salesman" algorithm, which determines the most efficient viewing route for presenting the FOIs in the reviewing station 122. The routing processor 136 then stores the x-y coordinates of the FOIs, along with the routing plan (which in the illustrated embodiment, is accomplished by simply placing the FOIs in a list in the order that they will be reviewed), in memory 134 for subsequent access by the reviewing station 122.

Referring still to FIG. 6, in one embodiment, a total of three reviewing stations 122 are shown coupled to the server 120, so that up to three cytotechnologists have simultaneous access to the pertinent information stored in the server 120. Notably, the system 10 can typically process the slides 112 much quicker than a cytotechnologist can review them. Even if the specimen processing speed of the system 110 is slower than the specimen review speed of a cytotechnologist, the system 110 can generally be operated 24 hours a day, whereas the typical cytotechnologist will only work 8 hours a day. Thus, the bottleneck in the screening process occurs at the human level, i.e., the detailed review of the biological material contained on the slides 112. Thus, it can be appreciated that the use of multiple reviewing stations 122 alleviates this bottleneck, thereby providing for a much more efficient process.

Figure 7:
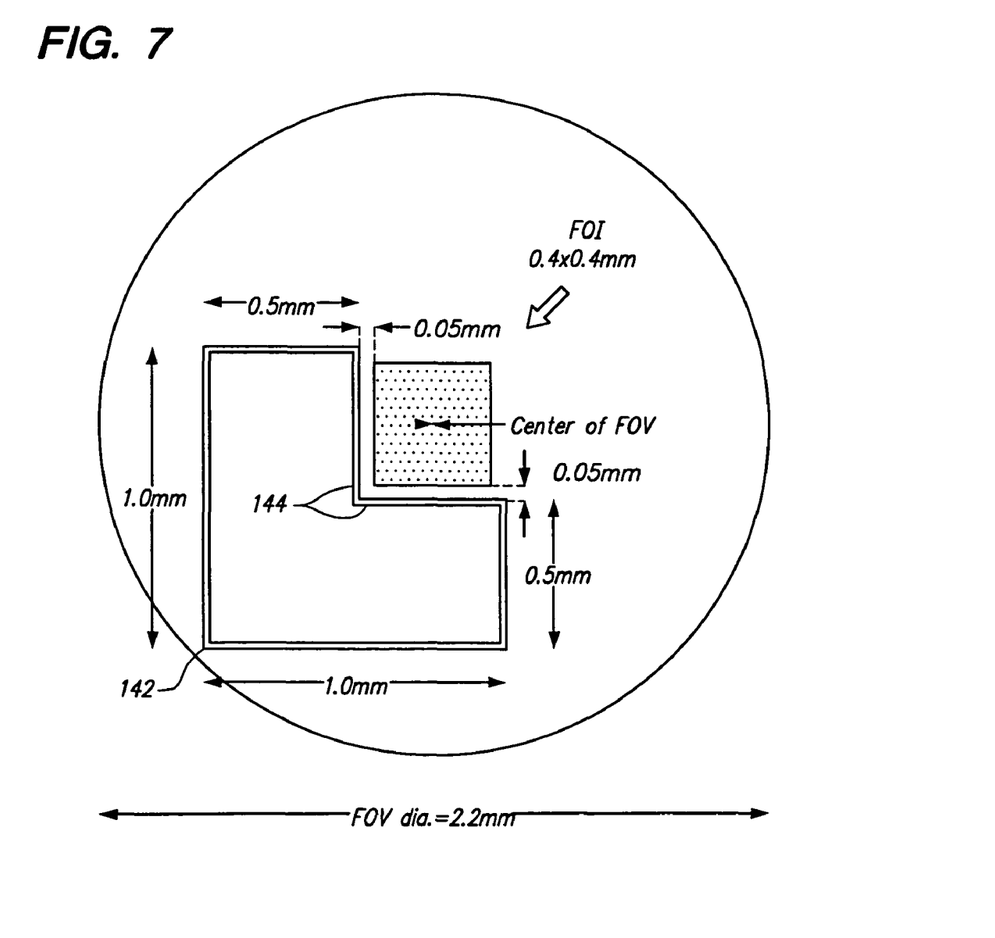
FIG. 7 is a view of a field of interest and marker indicator as shown through a field of view of a microscope used in the system of FIG. 5.

Before discussing the details of the reviewing stations 122, reference is made to FIG. 7, which illustrates an exemplary FOV that each reviewing station 122 centers over a FOI. In the illustrated embodiment, the FOV has a diameter of 2.2 mm, and the FOI is defined by a 0.4 mm×0.4 mm square circumscribed by the FOV. In the actual embodiment, the borders of the FOI are imaginary and cannot be seen, so that the cytotechnologist's view of any OOIs is not obstructed. In order to more quickly direct the cytotechnologist's attention to the FOI and to provide a reference that generally indicates the exact region bound by the imaginary borders of the FOI, an L-shaped mark indicator 142 is provided. The mark indicator 142 captures the FOI (i.e., an open square portion 144 of the mark indicator 142 borders the left and bottom sides of the FOI). A 0.05 mm margin is provided between the mark indicator 142 borders and the imaginary borders of the FOI, so that the portions of OOIs extending outside of the left and bottom borders of the FOI (resulting from an OOI that is included within the FOI, but centered near the left or bottom border of the FOI) will not be obstructed by the mark indicator 142. The mark indicator 142 also serves to provide a means for the cytotechnologist to electronically mark the FOI (e.g., by pushing a button that electronically colors the mark indicator 52) as requiring further review by a pathologist (e.g., if an OOI has malignant or pre-malignant attributes).

Referring back to FIG. 6, each reviewing station 122 comprises a microscope 138 and a motorized stage 140. The slide 112 (after image processing) is mounted on the motorized stage 140, which moves the slide 112 relative to the viewing region of the microscope 138 based on the routing plan and x-y coordinates of the FOIs obtained from memory 136. The slide 112 (after image processing) is mounted on the motorized stage 140, which moves the slide 112 relative to the viewing region of the microscope 138 based on the routing plan and a transformation of the x-y coordinates of the FOIs obtained from memory 138. Specifically, these x-y coordinates, which were acquired relative to the x-y coordinate system of the imaging station 118, will be transformed into the x-y coordinate system of the reviewing station 122 using the fiducial marks 116 affixed to the slide 112 (shown in FIG. 5). Thus, it is ensured that the x-y coordinates of the slide 112 during the reviewing process are correlated to the x-y coordinates of the slide 112 during the imaging process. The motorized stage 140 will then move in accordance with the transformed x-y coordinates of the FOIs, as dictated by the routing plan. In the illustrated embodiment, to advance from one FOI to another, the cytotechnologist presses an activation switch (not shown). In this sense, the reviewing station 122 is semi-automatic. Alternatively, the FOIs are automatically advanced from one to the next. In this case, the motorized stage 140 may optionally pause for a predetermined amount of time for each FOI. In this sense, the reviewing station 122 is fully automatic.

As the selected FOIs are presented in the FOV of the microscope 138, the cytotechnologist reviews the FOIs and makes decisions about the level of cell abnormality, if any. The cytotechnologist will then electronically mark FOIs that are suspect. The cytotechnologist is capable of returning to a previously viewed FOI, and manually moving to (and viewing) locations on the slide not encompassed by FOIs. Following review of the slide 112, if any of the FOIs have been marked by the cytotechnologist, the reviewing station 122 automatically scans the entire biological specimen 112, so that 100% viewing coverage is ensured. The cytotechnologist is able to pause the autoscan and to move the stage 140 in order to reposition and access locations on the slide 112, as desired.

Notably, the reviewing station 122 will apprise the cytotechnologist if the specimen 114 has been classified as suspicious (e.g., by providing an audible or visible signal) in which case, the cytotechnologist will prompted to perform a more thorough review of the slide 112 as compared to a review that the cytotechnologist would perform on a slide carrying a specimen that has been classified as normal.

The use of scatter plots can also be used to determine the quality of the stain on a batch of specimens. It has been discovered that biological specimens with low quality stains (e.g., the stain protocol has not been followed or the age of the stain has surpassed its shelf life and has deteriorated) tend to have a wider distribution in terms of both nuclear area and nuclear IOD (i.e., the scatter points tend to form a loosely bounded region). In contrast, biological specimens with high quality stains tend to have a narrow distribution in terms of both nuclear area and nuclear IOD (i.e., the scatter points tend to form a tightly bounded region). Thus, the spread of the scatter point distribution provides an indication of the quality of the stain on biological specimens 14 located on the slides 12. The difference between scatter plots generated from high quality and low quality stains stems from the fact that a low-quality stain is non-uniform, and thus will spread the scatter points away from the well-defined region otherwise resulting from a uniform and well-delineated nuclear to cytoplasmic contrast.

The scatter point distribution for each specimen can be quantified using any one of a variety of methods, but in the preferred embodiment, a geometric fit is performed on the scatter points and a value is computed in the same manner described above in determining whether a specimen is normal or suspicious. A combined value is then calculated from the values computed for a batch of specimens (e.g., 100 specimens), so that the stain quality of the specimen batch, as a whole, can be quantified. In the preferred embodiment, the median of the point distribution values for the specimens can be calculated. Alternatively, the median of point distribution values for a percentage of the specimens (e.g., the lowest 10 point distribution values) can be calculated. Rather than using the median, the mode or average of the point distribution values can be used.

Once the median value has been computed, it can be used to determine whether the current specimens have been properly stained. This can be accomplished in a variety of manners. For example, the median value can be compared with a baseline value computed (e.g., by taking the mean of point distribution values) from specimens that are known to be properly stained. Preferably, the number of specimens used to compute the baseline median value is large enough to provide a normal sampling of the specimens processed through the site at which the imaging system is located.

Assuming that the point distribution values are computed in a manner such that the values increase as the stain quality of the specimens decrease, a median value higher than the baseline value by a given amount will indicate that the current batch of specimens may have a low-quality stain. In this case, the image processor 22 will generate an error or a flag indicating that the recently analyzed specimens may not be properly stained. A subset of these suspect specimens may then be reviewed manually to visually confirm the quality of the stain.

Alternatively, a Chi-Square statistical method can be used for evalulating the median value of the current batch of specimens compared to the median values of previous batchs of specimens. For example, given the equation: $c^2 = \Sigma (f_o - f_e)^2 / f_e$, where $c^2$ equals the Chi-Square, $f_o$ equals the obtained mean values, and $f_e$ equals the expected mean value, it can be determined if the latest batch of specimens has a low-quality stain. For example, if the mean values of the last five batches of specimens are 130, 150, 110, 100, and 170, respectively, $f_e$ equals $$\frac{130 + 150 + 110 + 100 + 170}{5} = 132, \text{ and}$$

$$c^2 = \frac{(130-132)^2}{132} + \frac{(150-132)^2}{132} + \frac{(110-132)^2}{132} + \frac{(100-132)^2}{132} + \frac{(170-132)^2}{132}$$

$$= 0.0303 + 2.4545 + 3.6667 + 7.7575 + 10.9393$$

$$= 24.8483$$

Using a standard statistical handbook, the Chi-Square $c^2$ can then be compared to a cutoff value at a given confidence level to determine whether the mean values of the specimen batches fall within a normal distribution. If not, it is determined that the latest batch of specimens has a low-quality stain.

Alternatively, rather than determining a mean from the computed point distribution values, and then comparing that mean to a baseline value, the point distribution values can be directly compared with the baseline value. In this case, a number of the point distribution values that surpass the baseline value by a given number can be calculated, and compared to a threshold number. For example, if twenty percent of the point distribution values surpass the threshold value by the given number, it may be determined that the quality of the stain is suspect, thereby prompting the generation of an error or a flag.

Although particular embodiments of the present invention have been shown and described, it should be understood that the above discussion is not intended to limit the present invention to these embodiments. Those of ordinary skill in the art will appreciate that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for classifying a biological specimen, comprising:
  identifying a plurality of objects of interest (OOIs) within the biological specimen;
  measuring a nuclear area of each OOI;

measuring a nuclear integrated optical density of each OOI;

generating a scatter plot of the measured nuclear areas versus the nuclear integrated optical densities; and classifying the biological specimen as normal at least partially based on a distribution characteristic of points within the scatter plot, wherein the identifying, measuring, generating and classifying are performed by at least one image processor.

2. The method of claim 1, further comprising:

generating a series of images of the biological specimen; and processing the images to identify the plurality of OOIs.

3. The method of claim 1, further comprising skipping subsequent review of a specimen classified as normal.

4. The method of claim 1, comprising classifying the biological specimen as either normal or suspicious based on the point distribution.

5. The method of claim 4, further comprising skipping subsequent review of a specimen classified as normal, and performing a subsequent review of a specimen classified as suspicious.

6. The method of claim 5, further comprising generating a plurality of fields of interest (FOI) to include the OOIs if the biological specimen is classified as suspicious.

7. The method of claim 1, further comprising generating a standard from the biological specimen if the biological specimen is classified as normal.

8. A method for classifying a biological specimen, comprising:

identifying a plurality of objects of interest (OOIs) within the biological specimen;

measuring a first feature of each OOI;

measuring a second feature of each OOI;

generating a scatter plot of the first measured feature versus the second measured feature, the scatter plot having a distribution of points having a spread;

quantifying the spread of the point distribution; and classifying the biological specimen as normal at least partially based on a comparison of the quantified point distribution spread with a threshold value, wherein the identifying, measuring, generating, quantifying and classifying are performed by at least one image processor.

9. The method of claim 8, further comprising:

generating a series of images of the biological specimen; and processing the images to identify the plurality of OOIs.

10. The method of claim 8, further comprising skipping subsequent review of a specimen classified as normal.

11. The method of claim 8, comprising classifying the biological specimen as either normal or suspicious based on the point distribution.

12. The method of claim 11, further comprising skipping subsequent review of a specimen classified as normal, and performing a subsequent review of a specimen classified as suspicious.

13. The method of claim 12, further comprising generating a plurality of fields of interest to include the OOIs if the biological specimen is classified as suspicious.

14. The method of claim 8, further comprising generating a standard from the biological specimen if the biological specimen is classified as normal.

15. A biological screening system for classifying a biological specimen, comprising:

an imaging station for obtaining scanned images of the biological specimen, and generating image data from the scanned images; and at least one processor for filtering the image data to identify a plurality of objects of interest (OOIs) within the biological specimen, measuring a nuclear area of each OOI, measuring a nuclear integrated optical density of each OOI, generating a scatter plot of the measured nuclear areas versus the nuclear integrated optical densities, and classifying the biological specimen as normal at least partially based on a distribution characteristic of points within the scatter plot.

16. The biological screening system of claim 15, wherein the at least one processor is further for flagging a normal specimen as not requiring further review.

17. The biological screening system of claim 15, wherein the at least one processor is further for classifying the biological specimen as either normal or suspicious based on the point distribution.

18. The biological screening system of claim 17, wherein the at least one processor is further for flagging a normal specimen as not requiring further review, and flagging a suspicious specimen as requiring further review.

19. The biological screening system of claim 15, wherein the point distribution characteristic is a point distribution spread.

20. The biological screening system of claim 19, wherein the biological specimen is classified as normal if the point distribution spread is below a threshold.

21. The biological screening system of claim 19, wherein the at least one processor is further for quantifying the point distribution spread, defining a threshold value, and comparing the quantified point distribution spread to the threshold value, wherein the biological specimen is classified as normal based on the comparison.

22. The biological screening system of claim 21, wherein the at least one processor quantifies the point distribution spread by fitting a geometric shape to the points, determining at least one dimension of the geometric shape, and computing a value that is a function of the at least one dimension, and wherein the at least one processor compares the quantified point distribution spread to the threshold value by comparing the computed value to the threshold value.

23. The biological screening system of claim 22, wherein the geometric shape is an ellipse.

24. The biological screening system of claim 21, wherein the at least one processor quantifies the point distribution spread by computing a value, wherein the computed value is compared to the threshold value.

25. The biological screening system of claim 15, wherein the at least one processor is further for measuring at least one additional feature of the biological specimen, wherein the biological specimen is classified as normal based further on the at least one additional measured feature.

26. The biological screening system of claim 25, wherein the at least one processor is further for determining that the scatter plot is reliable based on the at least one additional measured feature.

27. The biological screening system of claim 25, wherein the at least one additional measured feature is a total number of OOIs in the biological specimen.

28. The biological screening system of claim 25, wherein the at least one additional measured feature is a total number of artifacts in the biological specimen.

29. The biological screening system of claim 25, wherein the at least one additional measured feature is a mean nuclear optical density of the OOIs.

30. The biological screening system of claim 15, wherein the number of OOIs is predetermined.

31. The biological screening system of claim 17, wherein the at least one processor is further for generating a plurality of fields of interest to include the OOIs if the biological specimen is classified as suspicious, the system further comprising an automated or semi-automated reviewing station for scanning a field of view relative to each field of interest to present the OOIs.

32. A biological screening system for classifying a biological specimen, comprising:
    an imaging station for obtaining scanned images of the biological specimen, and generating image data from the scanned images; and
    at least one processor for filtering the image data to identify a plurality of objects of interest (OOIs) within the biological specimen, measuring a first feature of each OOI, measuring a second feature of each OOI, generating a scatter plot of the first measured feature versus the second measured feature, the scatter plot having a distribution of points having a spread, quantifying the spread of the point distribution, and classifying the biological specimen as normal at least partially based on a comparison of the quantified point distribution spread with a threshold value.

33. The biological screening system of claim 32, wherein the at least one processor is further for flagging a normal specimen as not requiring further review.

34. The biological screening system of claim 32, wherein the at least one processor is further for a classifying the biological specimen as either normal or suspicious based on the point distribution.

35. The biological screening system of claim 34, wherein the at least one processor is further for flagging a normal specimen as not requiring further review, and flagging a suspicious specimen as requiring further review.

36. The biological screening system of claim 32, wherein the biological specimen is classified as normal if the quantified point distribution spread is below the threshold value.

37. The biological screening system of claim 32, wherein the at least one processor quantifies the point distribution spread by fitting a geometric shape to the points, determining at least one dimension of the geometric shape, and computing a value that is a function of the at least one dimension, and wherein the at least one processor compares the quantified point distribution spread to the threshold value by comparing the computed value to the threshold value.

38. The biological screening system of claim 37, wherein the geometric shape is an ellipse.

39. The biological screening system of claim 32, wherein the at least one processor quantifies the point distribution spread by computing a value, wherein the computed value is compared to the threshold value.

40. The biological screening system of claim 32, wherein the at least one processor is further for measuring at least one additional feature of the biological specimen, wherein the biological specimen is classified as normal based further on the at least one additional measured feature.

41. The biological screening system of claim 40, wherein the at least one processor is further for determining that the scatter plot is reliable based on the at least one additional measured feature.

42. The biological screening system of claim 40, wherein the at least one additional measured feature is a total number of the OOIs in the biological specimen.

43. The biological screening system of claim 40, wherein the at least one additional measured feature is a total number of artifacts in the biological specimen.

44. The biological screening system of claim 40, wherein the at least one additional measured feature is a mean nuclear optical density of the OOIs.

45. The biological screening system of, claim 32, wherein the number of OOIs is predetermined.

46. The biological screening system of claim 34, wherein the at least one processor is further for generating a plurality of fields of interest to include the OOIs if the biological specimen is classified as suspicious, the system further comprising an automated or semi-automated reviewing station for scanning a field of view relative to each field of interest to present the OOIs.

47. The biological screening system of claim 37, wherein the geometric shape is two-dimensional.

48. The biological screening system of claim 47, wherein the at least one dimension comprises two dimensions.

49. The biological screening system of claim 22, wherein the geometric shape is two-dimensional.

50. The biological screening system of claim 49, wherein the at least one dimension comprises two dimensions.

51. The method of claim 1, wherein the biological specimen is classified as normal based on a spread of the point distribution.

52. The method of claim 51, wherein the biological specimen is classified as normal if the point distribution spread is below a threshold.

53. The method of claim 51, further comprising quantifying the point distribution spread, defining a threshold value, and comparing the quantified point distribution spread to the threshold value, wherein the biological specimen is classified as normal based on the comparison.

54. The method of claim 53, wherein the point distribution spread is quantified by fitting a geometric shape to the points, determining at least one dimension of the geometric shape, and computing a value that is a function of the at least one dimension, and wherein the quantified point distribution spread is compared to the threshold value by comparing the computed value to the threshold value.

55. The method of claim 54, wherein the geometric shape is an ellipse.

56. The method of claim 53, wherein the point distribution spread is quantified by computing a value, wherein the computed value is compared to the threshold value.

57. The method of claim 1, further comprising measuring at least one additional feature of the biological specimen, wherein the specimen is classified as normal based further on the at least one additional measured feature.

58. The method of claim 57, further comprising determining that the scatter plot is reliable based on the at least one additional measured feature.

59. The method of claim 57, wherein the at least one additional measured feature is a total number of the OOIs in the biological specimen.

60. The method of claim 57, wherein the at least one additional measured feature is a total number of artifacts in the biological specimen.

61. The method of claim 57, wherein the at least one additional measured feature is a mean nuclear optical density of the OOIs.

62. The method of claim 1, wherein the number of OOIs is predetermined.

63. The method of claim 4, further comprising generating a plurality of fields of interest to include the OOIs if the biological specimen is classified as suspicious, and scanning a field of view relative to each field of interest to present the OOIs.

64. The method of claim 54, wherein the geometric shape is two-dimensional.

65. The method of claim 64, wherein the at least one dimension comprises two dimensions.

66. The method of claim 8, wherein the biological specimen is classified as normal based on a spread of the point distribution.

67. The method of claim 66, wherein the biological specimen is classified as normal if the quantified point distribution spread is below the threshold value.

68. The method of claim 8, wherein the point distribution spread is quantified by fitting a geometric shape to the points, determining at least one dimension of the geometric shape, and computing a value that is a function of the at least one dimension, and wherein the quantified point distribution spread is compared to the threshold value by comparing the computed value to the threshold value.

69. The method of claim 68, wherein the geometric shape is an ellipse.

70. The method of claim 8, wherein the point distribution spread is quantified by computing a value, wherein the computed value is compared to the threshold value.

71. The method of claim 8, further comprising measuring at least one additional feature of the biological specimen, wherein the specimen is classified as normal based further on the at least one additional measured feature.

72. The method of claim 71, further comprising determining that the scatter plot is reliable based on the at least one additional measured feature.

73. The method of claim 71, wherein the at least one additional measured feature is a total number of the OOIs.

74. The method of claim 71, wherein the at least one additional measured feature is a total number of artifacts in the biological specimen.

75. The method of claim 71, wherein the at least one additional measured feature is a mean nuclear optical density of the OOIs.

76. The method of claim 8, wherein the number of OOIs is predetermined.

77. The method of claim 11, further comprising generating a plurality of fields of interest to include the OOIs if the biological specimen is classified as suspicious, and scanning a field of view relative to each field of interest to present the OOIs.

78. The method of claim 68, wherein the geometric shape is two-dimensional.

79. The method of claim 78, wherein the at least one dimension comprises two dimensions.

80. The method of claim 1, further comprising performing the following steps with the at least one image processor:
 ranking the identified OOIs;
 selecting the highest ranked OOIs, wherein the nuclear area and nuclear integrated optical density of each selected OOI are measured.

81. The method of claim 8, further comprising performing the following steps with the at least one image processor:
 ranking the identified OOIs;
 selecting the highest ranked OOIs, wherein the first and second features of each selected OOI are measured.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,321,136 B2 | |
| APPLICATION NO. | : 10/794334 | |
| DATED | : November 27, 2012 | |
| INVENTOR(S) | : Wong et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1467 days.

Signed and Sealed this
Twenty-first Day of October, 2014

Michelle K. Lee
*Deputy Director of the United States Patent and Trademark Office*